(12) United States Patent
Hirshberg et al.

(10) Patent No.: US 8,038,868 B2
(45) Date of Patent: Oct. 18, 2011

(54) MICRO PH ELECTRODE (REFERENCE ELECTRODE)

(75) Inventors: Moshe Hirshberg, Brookline, MA (US); June Y. d'Heilly, Boston, MA (US)

(73) Assignee: Thermo Orion, Inc., Beverly, MA (US)

( * ) Notice: Subject to any disclaimer, the term of this patent is extended or adjusted under 35 U.S.C. 154(b) by 684 days.

(21) Appl. No.: 11/867,511

(22) Filed: Oct. 4, 2007

(65) Prior Publication Data

US 2008/0083620 A1  Apr. 10, 2008

Related U.S. Application Data

(60) Provisional application No. 60/849,417, filed on Oct. 4, 2006.

(51) Int. Cl.
*G01N 27/333* (2006.01)

(52) U.S. Cl. ............... 205/789; 205/787.5; 204/420

(58) Field of Classification Search ............... 205/787.5, 205/789; 204/416, 420
See application file for complete search history.

(56) References Cited

U.S. PATENT DOCUMENTS

| 3,530,056 | A | * | 9/1970 | Haddad | 204/435 |
| 3,880,737 | A | * | 4/1975 | Brunt | 204/420 |
| 6,793,787 | B1 | * | 9/2004 | Hirshberg et al. | 204/416 |

* cited by examiner

*Primary Examiner* — Jeffrey T Barton
*Assistant Examiner* — J. Christopher Ball
(74) *Attorney, Agent, or Firm* — Cesari and McKenna, LLP; Martin J. O'Donnell

(57) ABSTRACT

An improved combination ion-selective electrode has a thin ion-sensing body extending from an outer reference body. The exposed portion of the ion-sensing body is encompassed by a sleeve which effectively forms an extension of the reference body and also provides mechanical stability to the ion-sensing body. One or more fluid channels are formed interior to the sleeve to provide an electrically conductive path from the reference solution within the reference body to the tip of the electrode.

8 Claims, 2 Drawing Sheets

MICRO PH ELECTRODE (REFERENCE ELECTRODE)

CROSS-REFERENCE TO RELATED APPLICATIONS

The present application claims the benefit of U.S. Provisional Patent Application Ser. No. 60/849,417, which was filed on Oct. 4, 2006, by Moshe Hirshberg et al. for a MICRO PH ELECTRODE (REFERENCE ELECTRODE) and is hereby incorporated by reference.

BACKGROUND OF THE INVENTION

1. Field of the Invention

The invention relates to ion-selective electrodes and, specifically, to the structure and manufacture of an ion-specific electrode of compact size, yet including both sensing and reference electrodes.

2. Background Information

Ion-selective electrodes of various types are used to measure the concentration of ions in solution. Particularly useful electrodes are those which include both a sensing electrode and a reference electrode in a single unit; this type of electrode is commonly referred to as a "combination electrode". An example of such an electrode is described in U.S. Pat. No. 6,793,787, issued Sep. 21, 2004 to Moshe Hirshberg et al.

With the advent of large-scale testing of biological samples in very small sample vessels, a need has arisen for ion-selective electrodes which can be accommodated in such vessels. For example, one type of frequently-used sample vessel has 96 wells of dimensions 8 mm (millimeters) by 10 mm. The accommodation of ion-specific electrodes to such small volumes is challenging.

SUMMARY OF THE INVENTION

Accordingly, it is an object of the invention to provide an improved ion-selective electrode.

Further, it is an object of the invention to provide an improved combination ion-selective electrode.

A further object of the invention is to provide an improved combination ion-selective electrode that can be used for measuring ion-concentration in sample vessels in sample vessels of small size.

Still a further object of the invention is to provide an improved combination ion-selective electrode that can be used for measuring ion-concentration in sample vessels of small size and that is readily manufactured.

BRIEF DESCRIPTION OF THE DRAWINGS

The foregoing and other and further objects of the invention will be more readily understood on reference to the following detailed description of the invention when taken in connection with the accompanying drawings in which.

DETAILED DESCRIPTION OF AN ILLUSTRATIVE EMBODIMENT

Figure 1:
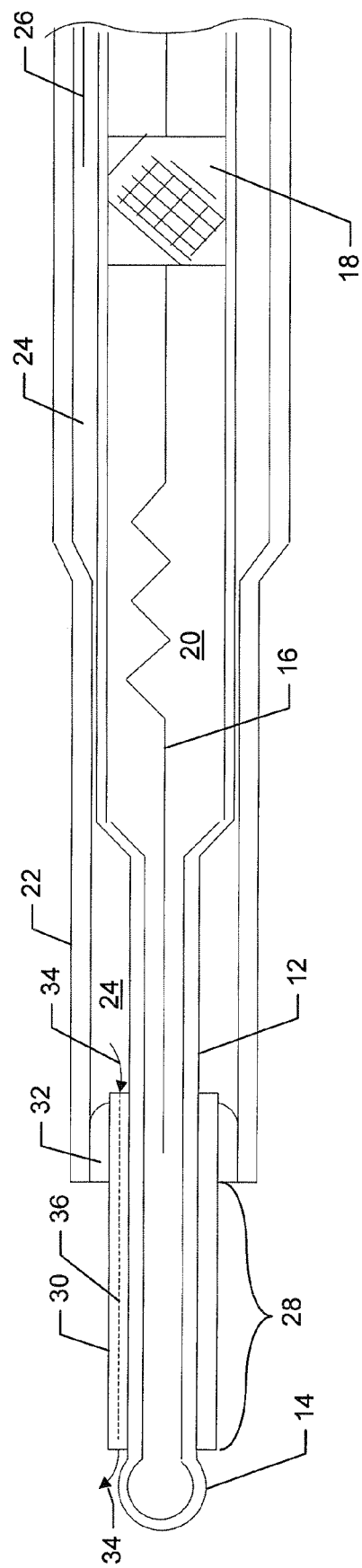
FIG. 1 is longitudinal sectional view of one embodiment of an electrode in accordance with the invention.

In FIG. 1, an ion-selective combination electrode 10 has a first body 12 ("the sensing body") in the form of a tube terminating at one end in an ion-selective membrane 14, for example, a pH-sensitive glass. The body 12 carries an electrical lead wire 16 which extends through a plug 18 to a measuring instrument (not shown) to enable measurement of the concentration of a specific ion (for example, $H^+$ ion) of a solution in which the electrode is immersed. A measuring solution (indicated as 20 but not otherwise shown) fills the interior of the body 12 between the membrane 14 and the plug 18. The lead wire 16 is immersed in this solution and thus in electrical contact with it.

The body 12 extends from a second body 22 ("the reference body"). A reference solution (not shown but indicated as 24) fills the interior of body 22 exterior to body 12. An electrical lead 26 immersed in the reference solution carries electrical signals from this solution to the measuring instrument.

The exposed portion 28 of the body 12 (i.e., that portion of body 12 extending out from body 22) is encompassed by a sleeve 30. As described more fully below, one or more fluid channels extending between the interior of body 22 and a location adjacent the membrane 14 are formed either in this sleeve, or in the body 12, or between the two of them. The channels carry reference solution 24 from the reference body to an area adjacent the membrane where the solution may be brought into contact with a sample to be tested when the tip of the body 12 is brought into contact with the sample. In this manner, an electrically conductive path is formed between the sample and the reference lead wire so that a reference potential may be established for the sample. The sleeve 30 extends into the reference body 22 a short distance. A bung seal 32 is fitted over the distal end of the sleeve to form a fluid-tight seal therewith and to firmly mount the sensing body within the reference body.

As noted above, fluid channels (indicated by arrows 34 and dotted lines 36) carry the reference solution 24 to the tip of the sensing electrode for contact with a sample together with the sensing electrode. The channels 30 may be formed in a variety of ways. For example, they may be cast, machined, molded or otherwise formed as narrow grooves or channels in either the sensing body 12, or the sleeve 30, or both, or may be formed by abrasion of one or the other at their interface. Further, they may be formed by one or more fibers or threads extending along the length of the sleeve. The fibers may be porous or non-porous. Similarly, the sleeve may be formed of any of a variety of materials, including glass, plastic (polymeric), or other materials.

In a preferred embodiment of the invention, we have formed the channels by laying glass fiber threads along the inside of a piece of shrinkable polymer tubing (preferably Teflon®) and then heat-shrinking the tubing over the sensing body 12, taking care to ensure that the threads extend fully from the distal end of the sleeve immersed in the reference filling liquid to the end adjacent the membrane 14 so as to form a continuous electrical path between the filling solution and the liquid in which the membrane (and the channel terminus or termini) is immersed for measurement. The threads locally distort the interface between the inner wall of the sleeve 30 and the outer wall of the sensing body 12 sufficiently to form the desired electrically conductive channels. In constructing the preferred embodiment described herein, we used fibers that protruded from both ends of the sleeve 30. We then heat-shrunk the sleeve onto the sensing body 12 and thereafter cut off the ends of the fibers that protruded beyond the sleeve. This method of forming the fluid channels is simple and inexpensive to implement.

In addition to providing a conductive path for measuring the reference potential, the sleeve helps to protect the sensing body from mechanical stress such as from bending or shock.

This is particularly important in the present invention, since the sensing body is of narrow width in relation to its length. Thus, we have constructed combination electrodes in which the sensing body is formed from a glass tube approximately 2.5 mm wide with a hemispherical membrane of the same diameter (2.5 mm) and whose length from the tip of the membrane to the beginning of body 22 is approximately 40 mm long. These electrodes are particularly well suited to ion measurements in small multi-well plates but, due to their size, are particularly susceptible to damage if handled carelessly. The aspect ratio (ratio of exposed length to width) of the particular embodiment described herein is 16, and the electrode can easily be damaged by bending forces that would be harmless in electrodes that are fatter and with a lower aspect ratio. The sleeve 30 aids considerably in preventing such damage.

Figure 2:
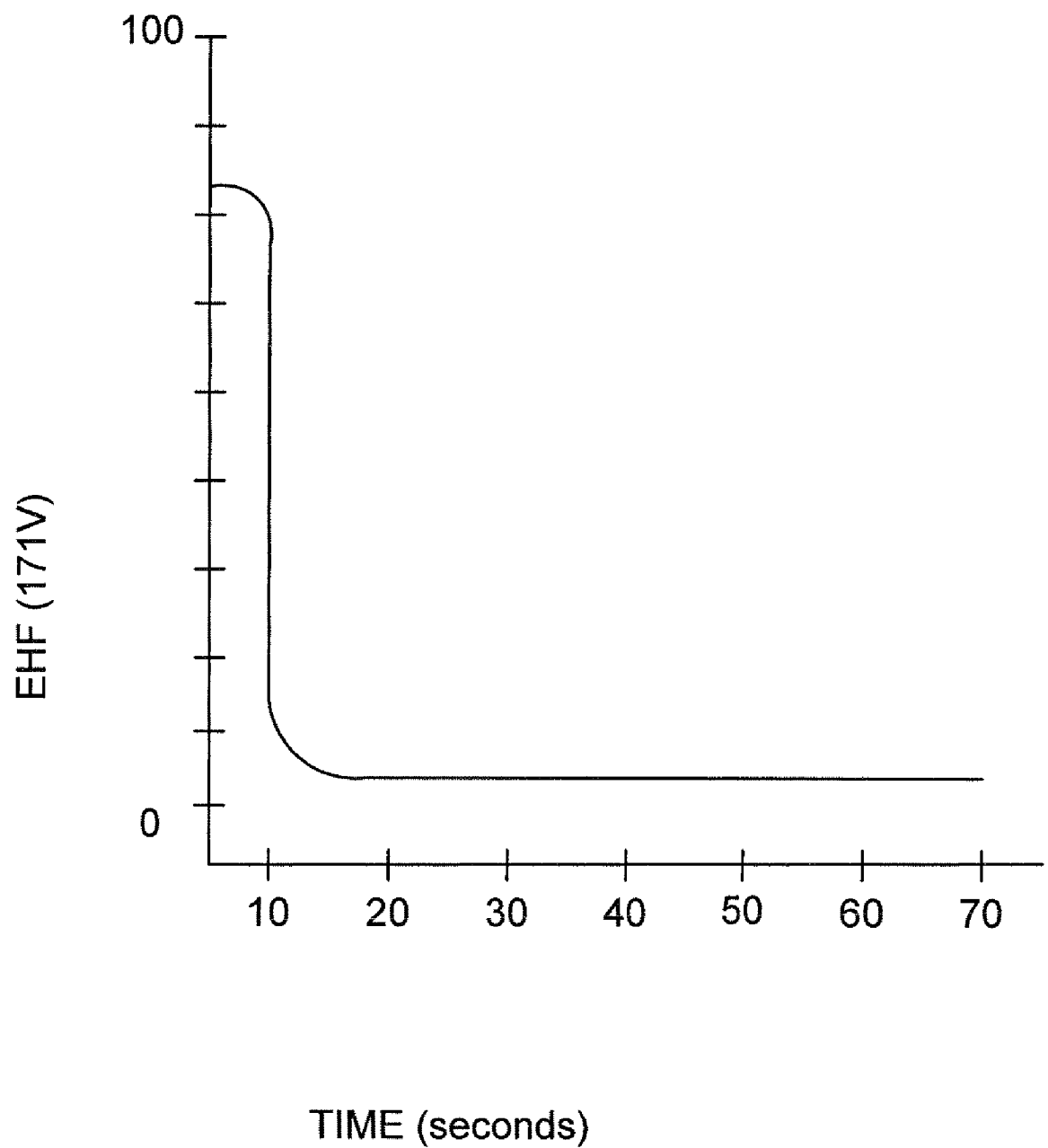
FIG. 2 is a graph showing the rapid response of the electrode of the present invention to immersion in a sample to be tested.

The present invention also advantageously accommodates the Ross® reference system for combination electrodes (see U.S. Pat. No. 6,793,787 noted above) and thus provides a rapid and highly stable response to immersion in a liquid to be measured. FIG. 2 shows an example of such performance. A combination electrode constructed in accordance with the present invention and using the Ross® reference system was immersed in a buffer solution (pH=7.0) and its response over time was monitored. As shown in FIG. 2, the output of the electrode settled to a long-term value of near zero volts within approximately 15 seconds of immersion. Tests showed that the response remained stable within approximately +/−15 millivolts over a temperature range of from 25 C (centigrade) to 70 C.

The electrode of the present invention may also advantageously be used in a combined ion-measuring and temperature-measuring system of the type set forth in U.S. Pat. No. 4,321,544, issued Mar. 23, 1982 to John H. Riseman. In such a system, the electrical resistance of the sensor membrane is measured simultaneous with the ion concentration. This resistance changes in accordance with the temperature of the solution in which the electrode is immersed, and thus the sensor measurement may readily and accurately be corrected for temperature.

CONCLUSION

From the foregoing, it will be seen that we have provided an improved ion-selective combination (sensing and reference) electrode. Due to the manner in which the electrically conductive path between the reference solution and the solution being tested is formed, the sensing end of the electrode is quite slender, and thus readily accommodates the small testing volumes and vessels now commonly found in the biotechnology industry, among others. It has rapid and stable response to immersion in a liquid to be tested, and is readily temperature compensated. It is easily, and thus inexpensively, manufactured.

What is claimed is:

1. A method of manufacturing a combination ion-selective electrode comprising:
    extending from a reference body a portion of a sensing electrode body of substantially smaller diameter than said reference body,
    encompassing said sensing electrode body with a sleeve for mechanically strengthening the extended portion of said sensing electrode body, and
    forming, at the interface between said sleeve and said sensing electrode body, one or more channels for passage of reference electrolyte through said channels to a point adjacent the tip of said sensing electrode body from a chamber exterior to said sleeve.

2. A method according to claim 1 in which said channels are formed by positioning one or more fibers at said interface to thereby locally deform said interface and thus provide said channels.

3. An ion-selective electrode for measuring a reference potential of a sample to be examined, comprising:
    a reference body surrounding a portion of a sensing body and having a first chamber intermediate said sensing body and said reference body for receiving reference solution therein;
    said sensing body having a portion thereof extending outwardly from said reference body and terminating in an ion-selective membrane, said sensing body having a second chamber on the interior thereof for receiving measuring solution therein;
    a sleeve surrounding said outwardly extending portion of said sensing body and terminating adjacent said membrane, said sleeve positioned at one end of said first chamber for receiving reference solution therefrom and providing, in conjunction with said sensing body, both an electrically conductive path between said first chamber and a sample when said sleeve is immersed in said sample and also providing mechanical strength to said sensing body.

4. An ion-selective electrode according to claim 3 in which said sleeve is formed of a heat-shrinkable polymeric material.

5. An ion-selective electrode according to claim 3 which includes one or more fibers extending along an inner wall of said sleeve from a first end to a second end thereof and positioned to contact said sensing body to thereby form said electrically conductive path.

6. An ion-selective electrode according to claim 3 in which the width of the exposed portion of said sensing body is less than 10 mm.

7. An ion-selective electrode according to claim 6 in which the width of the exposed portion of said sensing body is less than 3 mm.

8. An ion-selective electrode according to claim 3 in which said first portion is tubular and has a length that is at least ten times greater than its width.

* * * * *